United States Patent [19]

Franz

[11] 3,977,860
[45] Aug. 31, 1976

[54] HERBICIDAL COMPOSITIONS AND METHODS EMPLOYING ESTERS OF N-PHOSPHONOMETHYLGLYCINE

[75] Inventor: John E. Franz, Crestwood, Mo.

[73] Assignee: Monsanto Company, St. Louis, Mo.

[22] Filed: June 11, 1973

[21] Appl. No.: 368,805

Related U.S. Application Data

[60] Division of Ser. No. 170,385, Aug. 9, 1971, Pat. No. 3,799,758, which is a continuation-in-part of Ser. No. 123,057, March 10, 1971, abandoned.

[52] U.S. Cl. ........................................ 71/86; 71/87; 260/239 B; 260/247.1 B; 260/290 R; 260/293.88; 260/326.11 R; 260/326.61; 260/429.9; 260/438.1; 260/439 R; 260/551 P; 260/944; 260/945

[51] Int. Cl.$^2$ .......................................... A01N 9/36
[58] Field of Search ........................................ 71/86

[56] References Cited
UNITED STATES PATENTS

| | | | |
|---|---|---|---|
| 3,160,632 | 12/1964 | Fon Toy et al. | 424/211 X |
| 3,455,675 | 7/1969 | Irani | 71/86 |
| 3,728,381 | 4/1973 | Randall et al. | 71/86 |
| 3,733,192 | 5/1973 | Harris et al. | 71/86 |
| 3,799,758 | 3/1974 | Franz | 71/67 X |
| 3,853,530 | 12/1974 | Franz | 71/86 |

*Primary Examiner*—Glennon H. Hollrah
*Attorney, Agent, or Firm*—William T. Black

[57] ABSTRACT

N-phosphonomethylglycine and novel derivatives thereof useful as phytotoxicants or herbicides.

12 Claims, No Drawings

HERBICIDAL COMPOSITIONS AND METHODS EMPLOYING ESTERS OF N-PHOSPHONOMETHYLGLYCINE

This is a division of Ser. No. 170,385, filed Aug. 9, 1971, now U.S. Pat. No. 3,799,758 which was a continuation-in-part of application Ser. No. 123,057, filed Mar. 10, 1971, now abandonded.

This invention relates to novel N-phosphonomethylglycines which are useful as herbicides or phytotoxicants. This invention further relates to phytotoxicant compositions and to herbicidal methods.

The term "phytotoxicant" as used herein means materials which (1) effectively control all plants in a given locus or (2) selectively control the growth of one or more plant species in the presence of other plants. In like manner, "phytotoxic" and "phytotoxicity" are used to identify the overall and selective control activity of the compounds and compositions of this invention. The term "control" as used herein is inclusive of the actions of (1) killing, (2) inhibiting growth, reproduction or proliferation, and (3) removing, destroying or otherwise diminishing the occurrence and activity of plants and is applicable to any of the stated actions, or any combination thereof.

The term "plant" as used herein means terrestrial plants and aquatic plants.

The term "terrestrial plant" is inclusive of germinating seeds, emerging seedlings and herbaceous vegetation including the roots and above-ground portions, as well as established woody plants.

The term "aquatic plant" means algae and higher aquatic plants. The term "higher aquatic plant" means aquatic plants which are botanically higher than algae and is inclusive of vegetative organisms growing in water in which a major part of such organisms are normally largely submerged, e.g. roots as in Lemna, leaves as in Vallisneria or entire plants such as Anacharis. Thus, the term "higher aquatic plant" is inclusive of all water plants whether normally free-floating in their environing water such as Salvinia, or immersed species which are normally rooted in soil such as Vallisneria, as well as species which appear to grow normally in all respects either free-floating or rooted such as Anacharis or Alternanthera.

The N-phosphonomethylglycines of this invention are

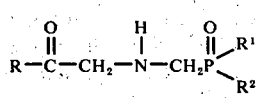

wherein R, $R^1$ and $R^2$ are independently selected from the group consisting of:

halogen; —OH; —SH;

—$NR^4R^5$ wherein $R^4$ and $R^5$ are independently selected from the group consisting of hydrogen, alkyl and hydroxyalkyl having 1 through 4 atoms, alkenyl having 2 through 4 carbon atoms, and $R^4$ and $R^5$ together with the nitrogen atom can form a heterocyclic ring;

—$OR^3$ and —$SR^3$ wherein $R^3$ is selected from the group consisting of monovalent hydrocarbon groups, monovalent hydrocarbonoxyhydrocarbon groups each containing from 1 to 18 carbon atoms, halogenated monovalent hydrocarbon groups, halogenated monovalent hydrocarbonoxyhydrocarbon groups each containing from 1 to 18 carbon atoms and from 1 to 3 halogens,

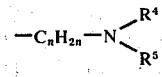

groups wherein $n$ is from 1 to 4 and $R^4$ and $R^5$ are as above defined provided that no more than two of R, $R^1$ or $R^2$ can be —$NR^4R^5$, —$OR^3$ or —$SR^3$; and —$OR^6$ wherein $R^6$ is a salt-forming cation selected from the group consisting of cations of alkali metals, alkaline earth metals, copper, zinc, manganese, nickel, ammonium, organic ammonium, provided that when the organic group is aryl the ammonium salt is a primary amine salt, and mixtures of such salts, provided that when any one of R, $R^1$ or $R^2$ is halogen the others of R, $R^1$ or $R^2$ cannot be —$OR^6$, and further provided that no more than two of R, $R^1$ or $R^2$ are —$OR^6$ when $R^6$ is ammonium or organic ammonium; and the strong acid salts of said compounds of the formula where R, $R^1$ and $R^2$ are —OH, said strong acid having a pK of 2.5 or less.

The term halogen as employed herein means chlorine, bromine, iodine and fluorine.

The term monovalent hydrocarbon as used herein includes alkyl, alkenyl, alkynyl, aralkyl inclusive of both straight and branched chain radicals, such as methyl, ethyl, isopropyl, cyclopropyl, cyclohexyl, tertiary butyl, n-butyl and the various forms of amyl, hexyl, heptyl, octyl, nonyl, decyl, undecyl, dodecyl, tridecyl tetradecyl, pentadecyl, hexadecyl, heptadecyl, octadecyl, benzyl, phenylethyl, naphthylethyl, tolylethyl, methylbenzyl, phenylbenzyl, and the corresponding alkenyl, and alkynyl groups and the like, aryl groups and alkaryl groups such as phenyl, tolyl, xylyl, naphthyl, vinylphenyl and the like. It is preferred that such monovalent hydrocarbon group contains from 1 to 18 carbon atoms and be alkyl, alkenyl, or alkynyl groups.

The monovalent hydrocarbonoxyhydrocarbon groups represented by $R^3$ include alkoxyalkyl, alkenoxyalkyl, alkoxyalkoxyalkyl, alkenoxyalkoxyalkyl, dialkoxyalkyl, alkenoxy(alkoxy)alkyl, alkenoxyalkoxy(alkoxy)alkyl, alkoxyalkoxy(alkoxy)alkyl, aryloxyalkyl and alkoxyaryl such as 2-methoxyethyl, 4-ethoxy-2-methyl-butyl, 2-ethoxyethyl, 3-propoxypropyl, 4-methoxybutyl, 4-methoxy-2-ethylbutyl, 4-butoxybutyl, 2-allyloxyethyl, 2-butenoxyethyl, 4-butenoxybutyl, 2-(2-methoxyethoxy)ethyl, 2-(2-butoxyethoxy)ethyl, 4-(3-methoxypropoxy)butyl, 2-(3-allyloxypropoxy)ethyl, 2-(2-butenoxyethoxy)ethyl, phenoxyethyl, naphthoxyethyl, butyl, 2,4-diethoxyphenyl, 2-methoxyphenyl, tolyloxyethyl, 4-phenoxybutyl, trifluoromethylphenyl, and the like.

Illustrative of the halogenated monovalent hydrocarbon groups represented by $R^3$ are haloalkyl such as chloromethyl, iodomethyl, bromomethyl, fluoromethyl, chloroethyl, iodoethyl, bromoethyl, 1,2-dichloroethyl, 1,2-diiodoethyl, 2,2-dibromoethyl, chloro-n-propyl, bromo-n-propyl, iodoisopropyl, bromo-n-butyl, bromo-tert-butyl, 1,3,3-trichlorobutyl, 1,3,3-tribromobutyl, chloropentyl, bromopentyl, 2,3-dichloropentyl, 3,3-dibromopentyl, chlorohexyl, bromohexyl, 2,4-dichlorohexyl, 1,3-dibromohexyl, 1,3,4-trichlorohexyl, chloroheptyl, bromoheptyl, fluoroheptyl, 1,3-dichloroheptyl, 1,4,4-trichloroheptyl, 2,4- dichloromethylheptyl, chlorooctyl, bromooctyl, iodooctyl, 2,4-dichloromethylhexyl, 2,4-dichlorooctyl, 2,4,4-trichloromethylpentyl, 1,3,5-tribromooctyl and the halogenated straight and branched chain nonyl, decyl, undecyl, dodecyl, tridecyl, tetradecyl, pentadecyl, hexadecyl, heptadecyl and octadecyl; haloalkenyl such as chlorovinyl, bromovinyl, chloroallyl, bromoallyl, 3-chloro-n-butenyl-1, 3-chloro-n-pentenyl-1, 4-chloro-n-hexenyl-2, 3,4-dichloromethylpentenyl-1, 3-fluoro-n-heptenyl-1, 1,3,3-trichloro-n-heptenyl-5, 1,3,5-trichloro-n-octenyl-6, 2,3,3-trichloromethylpentenyl-4 and the various homologues and isomers of haloalkenyl having 2 to 12 carbon atoms; haloaryl such as o-chlorophenyl, m-chlorophenyl, m-bromophenyl, p-chlorophenyl, 2,4-dichlorophenyl, 3,5-dichlorophenyl, 2,5-diiodophenyl, and the like. The halogenated monovalent hydrocarbonoxyhydrocarbon groups represented by $R^3$ are the alkoxy and aryloxy substituted derivatives of the foregoing halogenated monovalent hydrocarbon groups where the alkyl and aryl groups are those previously set forth.

The term "alkali-metal" encompasses lithium, sodium, potassium, cesium and rubidium; and the term "alkaline earth metal" includes beryllium, magnesium, calcium, strontium and barium.

The organic ammonium salts of the above formula are those prepared from low molecular weight organic amines, i.e. having a molecular weight below about 300, and such organic amines include the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-secbutylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine, primary aryl amines such as aniline, methoxyaniline, ethoxyaniline, o,m,p-toluidine, phenylenediamine, 2,4,6-tribromoaniline, benzidine, naphthylamine, o,m,p-chloroaniline, and the like; hetrocyclic amines such as pyridine, morpholine, piperidine, pyrrolidine, indoline, azepine and the like.

Among the preferred compounds of this invention are those of the above formula wherein at least one of R, $R^1$ and $R^2$ is $OR^3$ or $OR^6$ and the remaining members of R, $R^1$ and $R^2$ are OH, SH or $OR^6$. The more preferred compounds of this invention are those of the above formula wherein at least one of R, $R^1$ and $R^2$ is $OR^6$ and the remainder of R, $R^1$ and $R^2$ are OH, and wherein $R^6$ is a salt-forming cation. The particularly preferred compounds of this invention are those of the formula wherein one of R, $R^1$ and $R^2$ is $OR^6$, the remaining ones are OH, and $R^6$ is ammonium or organic ammonium wherein the organic ammonium group is selected from the group consisting of monoalkylammonium, dialkylammonium, trialkylammonium, monoalkenylammonium, dialkenylammonium, trialkenylammonium, monoalkynylammonium, dialkynylammonium, trialkynylammonium, monoalkanolammonium, dialkanolammonium, trialkanolammonium, heterocyclic ammonium or an aryl ammonium, such organic ammonium group containing from 1 to 18 carbon atoms.

One compound encompassed by the above formula, namely, N-phosphonomethylglycine, is known. This is the compound identified by the formula when each of R, $R^1$ and $R^2$ is —OH. The remainder of the compounds in accordance with the generic formula are new. All of the compounds of the present invention, however, are new and novel herbicides or phytotoxicants.

N-phosphonomethylglycine in itself is a very effective phytotoxicant or herbicide. Because it is relatively insoluble in water and conventional organic solvents, however, it is not as readily amenable to commercial formulation as are many of its derivatives. It is therefore generally preferred to utilize the more readily soluble compounds of this invention in which at least one of the hydrogens in the hydroxy or thiol groups of N-phosphonomethylglycine has been replaced with an alkali metal or an alkaline earth metal or has been combined with ammonia or an organic amine. The amino alkyl esters of N-phosphonomethylglycine are also efficacious phytotoxicants. Surprisingly, these and other compounds encompassed by the above general formula are water-soluble but yet exhibit the same high magnitude of activity as the glycine.

In addition, N-phosphonomethylglycine can be readily dehydrated to form linear and cyclic anhydrides which are also excellent phytotoxicants or herbicides.

The N-phosphonomethylglycines can be prepared by the phosphonomethylation of a glycine, preferably with chloromethylphosphonic acids. They also can be prepared by the phosphite addition to azomethines. For example, the reaction of ethyl glycinate with formaldehyde and diethylphosphite results in the formation of the triethyl ester of N-phosphonomethylglycine. Also, the compounds under consideration can be readily obtained by the oxidation of the corresponding aminophosphinic compounds utilizing mercuric chloride and other oxidizing agents. The N-phosphonomethylglycines are granular or crystalline solid materials generally soluble in water.

The strong acids which form salts with the N-phosphonomethylglycine are those having a pK of 2.5 or less, for example, hydrochloric acid, sulfuric acid, phosphoric acid, trifluoroacetic, trichloroacetic and the like. In some instances, these acid salts as isolated are the hemi-salt, i.e. one molecule of acid combines with 2 molecules of the N-phosphonomethylglycine and may contain water of hydration.

The acid halides of N-phosphonomethylglycine are prepared by known methods, for example chloro derivatives can be prepared by the reaction of N-phosphonomethylglycine with $PCl_5$ or $SOCl_2$ in an anhydrous solvent medium, such as an ether etc., or other organic solvent.

The amides, esters or thioesters of N-phosphonomethylglycine can be prepared by reacting the acid halide in a solvent with the appropriate amine, thiol, or alcohol in the presence of a hydrogen halide acceptor such as triethylamine, pyridine and the like; or by an ester interchange reaction with the methyl ester of N-phosphonomethylglycine.

The salts of N-phosphonomethylglycine are prepared by partial or complete neutralization of the acid with the appropriate base, basic carbonate, ammonia or organic amine.

In accordance with this invention it has been found that the growth of germinating seeds, emerging seedlings, maturing and established woody and herbaceous vegitation and aquatic plants can be controlled by exposing the emerging seedlings or above-ground portions of maturing and established vegetation, or the aquatic plants to the action of an effective amount of the glycines of the present invention. The compounds can be used individually, as admixtures of two or more compounds, or in admixture with an adjuvant. These compounds are effective as post-emergent phytotoxicants or herbicides, e.g., the selective control of the growth of one or more monocotyledonous species and-/or one or more dicotyledonous species in the presence of other monocotyledons and/or dicotyledones. Furthermore, these compounds are characterized by broad spectrum activity, i.e., they control the growth of a wide variety of plants including but not limited to ferns, conifer (pine, fir and the like), aquatic, monocotyledons and dicotyledons.

In the following examples, which illustrate the invention, and throughout the specification, parts and percent are by weight unless otherwise indicated.

EXAMPLE 1

A mixture of about 50 parts of glycine, 92 parts of chloromethylphosphonic acid, 150 parts of 50% aqueous sodium hydroxide and 100 parts water was introduced into a suitable reaction vessel and maintained at reflux temperature while an additional 50 parts of 50% aqueous sodium hydroxide was added. The pH of the reaction mixture was maintained between 10 and 12 by the rate of addition of the sodium hydroxide. After all of the caustic solution had been added, the reaction mixture was refluxed for an additional 20 hours, cooled to room temperature and filtered. About 160 parts of concentrated hydrochloric acid were then added and the mixture filtered to provide a clear solution which slowly deposited N-phosphonomethylglycine. This material had a melting point of 230°C with decomposition.

Calc'd. for $C_3H_8NO_5P$: C, 21.31; H, 4.77; N, 8.28. Found: C, 21.02; H, 5.02; N, 8.05.

EXAMPLE 2

N-phosphonomethylglycine was also prepared by the oxidation of N-phosphinomethylglycine in accordance with the following method:

A mixture of about 107 parts of phosphinomethylglycine, 625 parts of mercuric chloride and 50 parts of water were charged into a suitable reaction vessel and maintained at reflux temperature for about two hours. The mercurous chloride resulting from the reaction precipitated out and was removed by filtration. The filtrate was saturated with hydrogen sulfide and the resultant mercuric sulfide removed therefrom by filtration to provide a clear filtrate which was concentrated at reduced pressure and the residue diluted with 10 parts of water. The crystalline prpecipitate was collected and washed with methanol and then with diethyl ether. The product thus obtained was identical to the product of the preceding example.

EXAMPLE 3

A mixture of about 17 parts of N-phosphonomethylglycine, 100 parts of water and 7 parts of potassium carbonate was agitated in a suitable reaction vessel at room temperature. After dissolution was complete as indicated by clarification of the reaction mixture, the reaction mixture was concentrated on a steam bath at reduced pressure. The residue was washed with hot methanol and then with diethyl ether. The product thus obtained is the monopotassium salt of N-phosphonomethylglycine hemihydrate.

Calc'd. for $C_3H_7NO_5PK.1/2H_2O$: C, 16.65; H, 3.70; N, 6.46 Found: C, 16.67; H, 3.85; N, 6.32

By increasing the amount of potassium carbonate used, the corresponding dipotassium and tripotassium salts of N-phosphonomethylglycine can be prepared. Corresponding ammonium salts and salts of other alkali metal and alkaline earth metal salts as well as copper, zinc, manganese and nickel salts are readily prepared in substantially the same manner.

Following the above procedure, the following salts of N-phosphonomethylglycine were obtained as white powders:

Mono-, di-, and trisodium salts;
Mono-, di-, and trilithium salts.

EXAMPLE 4

About 170 parts of N-phosphonomethylglycine were added to a solution of 45 parts of dimethylamine dissolved in 10 parts of water and contained in a suitable reaction vessel. The reaction mixture cleared within a short period of time while the mixture was subject to agitation. The resulting solution was then concentrated by heating to 100°C. at reduced pressure. The residue was a viscous oil from which a crystalline solid was obtained. The product was identified as the mono-dimethylamine salt of N-phosphonomethylglycine, m.p. 150°C. with decomposition.

Calc'd. for $C_5H_{15}N_2O_5P$: C, 28.04; H, 7.06; N, 13.08; P, 14.66. Found: C, 27.88; H, 6.92; N, 12.88; P, 14.22.

Following the above procedure, other amine salts of N-phosphonomethylglycine can be prepared, e.g., the pyridine salts (monosalt - white solid), the diethylamine salts, the morpholine salts, the piperidine salts, ethanol amine salt (deliquescent powder to viscous liquid), ammonium salt (white powder).

EXAMPLE 5

Gaseous hydrogen chloride was led through a suspension of 6 g. (0.0355 mole) of N-phosphonomethylglycine in excess methyl alcohol until a clear solution was obtained. The solution was concentrated at reduced pressure and the residue mixed with a solution of methanol containing at least one equivalent of triethylamine. The solvent was removed at reduced pressure and the residue extracted with ether until granular. The granular solid was finally extracted with methanol to remove triethylamine hydrochloride. The insoluble product, methyl N-phosphonomethylglycinate, was obtained in excellent yield. After recrystallization from dilute methanol, the product melted with decomposition at 208.5°C.

Calc'd. for $C_4H_{10}NO_5P$: C, 26.24; H, 5.50. Found: C, 26.15; H, 5.43.

The following esters were prepared according to the above procedure (all melt with decomposition at the temperature indicated):

| | |
|---|---|
| dodecyl N-phosphonomethylglycinate | 197–200°C. |
| chloroethyl N-phosphonomethylglycinate | 207°C. |
| ethyl N-phosphonomethylglycinate | 203°C. |
| cyclohexyl N-phosphonomethylglycinate | 195°C. |
| decyl N-phosphonomethylglycinate | 201–204°C. |
| hexyl N-phosphonomethylglycinate | 202°C. |
| octyl N-phosphonomethylglycinate | 200°C. |
| n-butyl N-phosphonomethylglycinate | 207–209°C. |
| propyl N-phosphonomethylglycinate | 208.5°C. |

EXAMPLE 6

A mixture of 10 g. (0.055 mole) of methyl N-phosphonomethylglycinate and excess concentrated aqueous ammonium hydroxide was heated at the reflux temperature for two hours. The solution was then concentrated at reduced pressure, the residue washed with ether and methanol, and the granular product stirred with a mixture of excess glacial acetic acid in methanol. The precipitated solid was collected, washed with methanol and crystallized from dilute ethanol. The yield of N-phosphonomethylglycinamide, m.p. 227°C. with decomposition; was 8 g. or 87% of the theoretical amount.

Calc'd. for $C_3H_9N_2O_4P$: C, 21.44; H, 5.40 Found: C, 21.26; H, 5.39

EXAMPLE 7

A solution of 16.9 g. (0.10 mole) of N-phosphonomethylglycine in 300 mls. of hot water was heated at the reflux temperature with 5.6 g. (0.10 mole) calcium oxide. After about ten minutes, the mixture was cooled and filtered. The residue was washed with methanol and ether. After air-drying, the yield of calcium salt of N-phosphonomethylglycine hydrate was 17.5 g. or 84% of the theoretical yield.

Calc'd. for $C_3H_6NO_5PCa.2½ H_2O$: C, 13.73; H, 4.05; Ca, 15.76. Found: C, 13.75; H, 4.20; Ca, 15.28.

EXAMPLE 8

A mixture of 17 g. (0.10 mole) of N-phosphonomethylglycine and 2 g. (0.05 mole) of magnesium oxide in 300 mls. of water was heated at the reflux temperature for ten minutes. The solution was cooled to room temperature and filtered to remove a small amount of sediment. The clear filtrate was then concentrated at reduced pressure and the granular residue washed with methanol and ether. Magnesium bis-N-phosphonomethylglycinate hydrate was obtained in excellent yield.

Calc'd. for $C_6H_{14}N_2O_{10}P_2Mg.2½ H_2O$: C, 17.79; H, 4.57; Mg, 5.56. Found: C, 17.80; H, 4.69; Mg, 6.00.

EXAMPLE 9

A mixture of 20 g. (0.11 mole) of methyl N-phosphonomethylglycinate and about 23 g. (0.33 mole) of pyrrolidine was heated on a steam bath for two hours. Excess amine was then removed at reduced pressure and the residue washed with ether and tetrahydrofuran. The gummy product was stirred with a mixture of excess glacial acetic acid in methanol and the crystalline precipitate collected by filtration. After washing with methanol and ether, the tetramethylene N-phosphonomethylglycinamide, m.p. 243°C. with decomposition, was obtained in a yield of 12 g. or 49% of the theoretical amount. The product was recrystallized from dilute ethanol for analysis.

Calc'd. for $C_7H_{15}N_2O_4P$: C, 37.84; H, 6.81 Found: C, 37.82; H, 6.96

EXAMPLE 10

N-phosphonomethylglycine (10 g.) was placed in a small beaker and covered with concentrated hydrochloric acid (approximately 5 ml.). After the exothermic reaction has subsided, the mixture was allowed to stand about 10 to 15 minutes. The crystalled solid was washed with tetrahydrofuran and then air-dried to yield an essentially quantitative yield of N-phosphonomethylglycine hemihydrochloride hemihydrate (m.p. greater than 300°C.).

Other compounds of the present invention that can be made in general accordance with the foregoing procedure include:

N-chlorophosphonylmethylglycine
N-dichlorophosphonylmethylglycine
N-phosphonomethylglycinyl chloride
N-phosphonomethylglycinyl bromide
N-phosphonomethylglycinyl iodide
N-phosphonomethylglycinyl fluoride
N-dichlorophosphonylmethylglycinyl chloride
N-dibromophosphonylmethylglycine
N-diiodophosphonylmethylglycine
Monopyridine salt of N-phosphonomethylglycine
Monobutylamine salt of N-phosphonomethylglycine
Mono-(trimethylamine) salt of N-phosphonomethylglycine
Monopyrrolidine salt of N-phosphonomethylglycine
Mono(diethylenetriamine) salt of N-phosphonomethylglycine
Monoisopropylamine salt of N-phosphonomethylglycine
Mono-n-propylamine salt of N-phosphonomethylglycine
Monomorpholine salt of N-phosphonomethylglycine
Mono(dipropargylamine) salt of N-phosphonomethylglycine
Monosodium salt of ethyl N-phosphonomethylglycinate
Potassium salt of ethyl N-phosphonomethylglycinate
Mono(dialkylamine) salt of N-phosphonomethylglycine
Monolithium salt of ethyl-N-phosphonomethylglycinate
Monosodium salt of propyl-N-phosphonomethylglycinate
Monosodium salt of methyl-N-phosphonomethylglycinate
Monosodium salt of chloroethyl-N-phosphonomethylglycinate
Monosodium salt of hexyl-N-phosphonomethylglycinate
Monopotassium salt of methyl-N-phosphonomethylglycinate
Monopotassium salt of propyl-N-phosphonomethylglycinate
Monopotassium salt of butyl-N-phosphonomethylglycinate
Monopotassium salt of hexyl-N-phosphonomethylglycinate
Monopotassium salt of chloroethyl-N-phosphonomethylglycinate
Mono(picoline) salt of N-phosphonomethylglycine Monocyclohexylamine salt of N-phosphonomethylglycine
Di(methylamine) salt of N-phosphonomethylglycine
Di(dimethylamine) salt of N-phosphonomethylglycine
Di(ethylamine) salt of N-phosphonomethylglycine
Di(n-propylamine) salt of N-phosphonomethylglycine
Di(iso-propylamine) salt of N-phosphonomethylglycine
Di(morpholine) salt of N-phosphonomethylglycine
Mono(oleylamine) salt of N-phosphonomethylglycine
Mono(steaylamine) salt of N-phosphonomethylglycine
Mono(tallowamine) salt of N-phosphonomethylglycine
Mono(methylbutylamine) salt of N-phosphonomethylglycine
N-difluorophosphonylmethylglycine
N-phosphonomethylglycine hemihydrobromide hemihydrate
N-phosphonomethyl thiolglycine
N-thiolphosphonomethylglycine
N-dithiolphosphonomethylglycine
chloropropyl-N-phosphonomethylglycine
N-trithiolphosphonomethylglycine
phenyl-N-phosphonomethylglycinate
naphthyl-N-phosphonomethylglycinate
methoxyethyl-N-phosphonomethylglycinate
dimethyl-N-(phosphonomethyl)glycinate
methyl-N-phosphonomethyl thiolglycine
decyl-N-phosphonomethyl thiolglycine
octadecyl-N-phosphonomethyl thiolglycine
N,N-dimethyl(N-phosphonomethyl)glycinamide
N,N-dibutyl(N-phosphonomethyl) glycinamide monosodium salt
N-(phosphonomethyl)glycine monoethylamine salt
dichloroethyl-N-(phosphonomethyl)glycinate
trichlorobutyl-N-(phosphonomethyl)glycinate
dibromohexyl-N-(phosphonomethyl)glycinate
trifluoromethylphenyl-N-(phosphonomethyl)glycinate
dichlorophenyl-N-(phosphonomethy)glycinate
dibutylamine salt of N-(phosphonomethyl)glycine
octadecylamine salt of N-(phosphonomethyl)glycine
methoxyethylamine salt of N-(phosphonomethyl) glycine
ethylenediamine salt of N-(phosphonomethyl)glycine
pyrrolidine salt of N-(phosphonomethyl)glycine
dipropanolamine salt of N-(phosphonomethyl)glycine
chloroethylamine salt of N-(phosphonomethyl)glycine
phenoxyethylamine salt of N-(phosphonomethyl)glycine
N,N-diethylaminoethyl-N-(phosphonomethyl)glycinate

EXAMPLE 11

In order to demonstrate the phytotoxic activity of the compounds of this invention against aquatic species, alligator weed (*Alternanthera philoperorides*) was sprayed with an aqueous solution of N-phosphonomethylglycine at the rate of 0.125 pound per acre. The plants were maintained under greenhouse conditions for four weeks and the response of the plants was then noted. At the end of the four week period, all of the plants were dead. Control plants were normal after 4 weeks.

EXAMPLE 12

The post-emergence herbicidal activity of various compounds of this invention is demonstrated as follows. The active ingredients are applied in spray form to 14 or 21 day old specimens (as indicated) of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (pounds per acre) of active ingredient. The treated plants are placed in a greenhouse and the effects are observed and recorded after approximately 2 weeks or approximately 4 weeks, as is indicated in the last column of Table I.

The post-emergence herbicidal activity index used in Table I is as follows:

| PLANT RESPONSE | INDEX | PLANT RESPONSE | INDEX |
|---|---|---|---|
| No injury | 0 | Severe injury | 3 |
| Slight injury | 1 | Killed | 4 |
| Moderate injury | 2 | | |

The plant species utilized in these tests are identified by letter in accordance with the following legend:

| | |
|---|---|
| A — Soybean | K — Smartweed |
| B — Sugar Beet | L — Velvetleaf |
| C — Wheat | M — Downy Brome |
| D — Rice | N — Panicum Spp |
| E — Sorghum | O — Barnyardgrass |
| F — Cocklebur | P — Crabgrass |
| G — Wild Buckwheat | Q — Nutsedge* |
| H — Morningglory | R — Quackgrass* |
| I — Hemp sesbania | S — Johnsongrass* |
| J — Lambsquarters | T — Canada thistle* |

*Established from vegetive propagules.

TABLE I

| COMPOUND | RATE | A | B | C | D | E | F | G | H | I | J | K | L | M | N | O | P | Q | R | S | T | WEEKS |
|---|---|---|---|---|---|---|---|---|---|---|---|---|---|---|---|---|---|---|---|---|---|---|
| I | 4 | — | — | — | — | — | 4 | — | 2 | — | 4 | — | 4 | 4 | — | 4 | — | 4 | 3 | 4 | — | 2 |
| I | 1 | 0 | 1 | 3 | 1 | 3 | 2 | 1 | 2 | 0 | 2 | — | 1 | 3 | 4 | 3 | 3 | — | — | — | — | 4 |
| II | 4 | — | — | — | — | — | 4 | — | 3 | — | 4 | 4 | 4 | 4 | — | 4 | — | 4 | 4 | 4 | — | 2 |
| II | 1 | 3 | 4 | 4 | 3 | 4 | 3 | 2 | 3 | 3 | 4 | — | 4 | 4 | 4 | 4 | 4 | — | — | — | — | 4 |
| III | 4 | — | — | — | — | — | 4 | — | 4 | — | 4 | — | 4 | 4 | — | — | — | 4 | 4 | 3 | — | 4 |
| III | 1 | 3 | 4 | 4 | 4 | 4 | 4 | 1 | 2 | 3 | 4 | 4 | 3 | 3 | 4 | 4 | 4 | — | — | — | — | 2 |
| IV | 4 | — | — | — | — | — | 4 | — | 3 | — | 4 | — | 4 | 4 | — | — | — | 4 | 4 | 4 | 4 | 4 |
| IV | 1 | 3 | 4 | 3 | 4 | 4 | 4 | 3 | 3 | 4 | 4 | — | 4 | 4 | 4 | 4 | 4 | — | — | — | — | 2 |
| V | 4 | — | — | — | — | — | 4 | — | 3 | — | 4 | — | 4 | 4 | — | — | — | 4 | 4 | 4 | — | 4 |
| V | 1 | 2 | 4 | 4 | 4 | 4 | 4 | 2 | 2 | 3 | 4 | — | 3 | 4 | 4 | 4 | 4 | — | — | — | — | 2 |
| VI | 4 | — | — | — | — | — | 4 | — | 4 | — | 4 | 4 | 4 | — | 4 | — | 4 | 4 | 4 | 4 | 4 | |
| VI | 1 | 3 | 4 | 4 | 3 | 4 | 4 | 3 | 2 | 4 | 4 | — | 3 | 4 | 4 | 4 | 4 | — | — | — | — | 2 |
| VII | 4 | — | — | — | — | — | 3 | — | 1 | — | 3 | 2 | 2 | 2 | — | 3 | — | 1 | 2 | 3 | 2 | 2 |
| VIII | 4 | — | — | — | — | — | 3 | — | 2 | — | 3 | $ | 3 | 3 | — | 3 | — | 2 | 4 | 3 | — | 2 |
| IX | 4 | — | — | — | — | — | 3 | — | 3 | — | 4 | 4 | 3 | 3 | — | 3 | — | 2 | 4 | 3 | — | 2 |
| X | 4 | — | — | — | — | — | 3 | — | 3 | — | 4 | 4 | 4 | 4 | — | 4 | — | 3 | 4 | 4 | 4 | 2 |
| XI | 4 | — | — | — | — | — | 4 | — | 3 | — | 4 | 4 | 4 | 3 | — | 4 | — | 3 | 3 | — | 4 | 2 |

TABLE I-continued

| COMPOUND | RATE | A | B | C | D | E | F | G | H | I | J | K | L | M | N | O | P | Q | R | S | T | WEEKS |
|---|---|---|---|---|---|---|---|---|---|---|---|---|---|---|---|---|---|---|---|---|---|---|
| XII | 4 | — | — | — | — | — | 4 | — | 3 | — | 4 | 4 | 4 | — | 4 | — | 2 | 4 | — | 4 | 4 |
| XIII | 4* | — | — | — | — | — | 4 | — | 2 | — | 3 | — | 3 | 1 | — | 3 | — | 1 | 2 | 1 | 3 | 2 |
| XIV | 4* | 0 | 3 | 2 | 2 | 1 | 1 | 0 | 2 | — | — | — | 1 | 0 | 3 | 3 | 3 | — | — | — | — | 2 |
| XV | 10* | — | — | — | — | — | 1 | — | 1 | — | 4 | — | — | 2 | — | 4 | — | 1 | 4 | 2 | 0 | 2 |
| XVI | 4* | — | — | — | — | — | 2 | — | 2 | — | 3 | 2 | 3 | 2 | — | 2 | — | 1 | 0 | 2 | 2 | 2 |
| XVII | 4 | — | — | — | — | — | 4 | — | 3 | — | 4 | — | 4 | 4 | — | 4 | — | 4 | 4 | 4 | 4 | 2 |
| XVIII | 4 | — | — | — | — | — | 3 | — | 1 | — | 4 | — | 3 | 3 | — | 3 | — | 2 | 3 | 3 | — | 2 |
| XIX | 4 | — | — | — | — | — | 3 | — | 2 | — | 3 | — | 3 | 3 | — | 2 | — | 2 | 3 | 4 | — | 2 |
| XX | 4 | — | — | — | — | — | 4 | — | 3 | — | 4 | — | 4 | 3 | — | 4 | — | 3 | 4 | 4 | 4 | 2 |
| XXI | 4 | — | — | — | — | — | 4 | — | 3 | — | 4 | — | 3 | 3 | — | 3 | — | 4 | 4 | — | 4 | 2 |
| XXII | 4 | — | — | — | — | — | 3 | — | 1 | — | 4 | — | 4 | 3 | — | 2 | — | 2 | 1 | 4 | 3 | 2 |
| XXIII | 4 | — | — | — | — | — | 4 | — | 3 | — | 4 | — | 3 | 3 | — | 4 | — | 4 | 4 | 4 | 4 | 2 |
| XXIV | 4 | — | — | — | — | — | 4 | — | 2 | — | 4 | — | 3 | 4 | — | 4 | — | 3 | 4 | 4 | — | 2 |
| XXV | 4 | — | — | — | — | — | 4 | — | 2 | — | 4 | — | 4 | 4 | — | 4 | — | 4 | 4 | 4 | 4 | 2 |
| XXVI | 4 | — | — | — | — | — | 4 | — | 3 | — | 4 | — | 4 | 3 | — | 4 | — | 4 | 4 | 4 | 4 | ** |
| XXVII | 4 | — | — | — | — | — | 4 | — | 2 | — | 4 | — | 4 | 3 | — | 4 | — | 3 | 4 | 2 | 1 | ** |
| XXVIII | 4 | — | — | — | — | — | 4 | — | 3 | — | 4 | — | 4 | 2 | — | 4 | — | 4 | 4 | 4 | 3 | ** |
| XXIX | 4 | — | — | — | — | — | 4 | — | 4 | — | 4 | — | 4 | 4 | — | 4 | — | 4 | 4 | 4 | 4 | 2 |
| XXX | 4 | — | — | — | — | — | 4 | — | 4 | — | 4 | — | 4 | 4 | — | 4 | — | 4 | 4 | — | 4 | 2 |
| XXXI | 4 | — | — | — | — | — | 4 | — | 4 | — | 4 | — | 4 | 4 | — | 4 | — | 4 | 4 | — | 4 | 2 |
| XXXII | 4 | — | — | — | — | — | 4 | — | 4 | — | 4 | — | 4 | 4 | — | 4 | — | 4 | 4 | — | 4 | 2 |

*Applied to 3-week old plants. All other tests conducted on 2-week old plants.
**These readings made after 11 days.

The following are the compounds referred to by the Roman numerals in the table:

| ROMAN NUMERAL | COMPOUND NAME |
|---|---|
| I | N-phosphonomethylglycine |
| II | Sodium N-phosphonomethylglycinate |
| III | Disodium N-phosphonomethylglycinate |
| IV | Trisodium N-phosphonomethylglycinate |
| V | N-Phosphonomethylglycine, mono-ethanolamine salt |
| VI | N-Phosphonomethylglycine, mono-ammonium salt |
| VII | Monohydrate calcium salt of N-phosphonomethylglycine |
| VIII | Magnesium salt of N-phosphonomethylglycine |
| IX | Magnesium bis-(N-phosphonomethylglycinate) |
| X | Potassium salt of N-phosphonomethylglycine |
| XI | Dimethylamine salt of N-phosphonomethylglycine |
| XII | Copper bis-(N-phosphonomethylglycinate) |
| XIII | Dilithium salt of N-phosphonomethylglycine |
| XIV | Zinc salt of N-(phosphonomethyl)glycine |
| XV | N-Phosphonomethylglycinamide |
| XVI | Methyl-N-(phosphonomethyl)glycinate |
| XVII | Ethyl-N-(phosphonomethyl)glycinate |
| XVIII | n-propyl-N-(phosphonomethyl)glycinate |
| XIX | n-butyl-N-(phosphonomethyl)glycinate |
| XX | n-hexyl-N-(phosphonomethyl)glycinate |
| XXI | Cyclohexyl-N-(phosphonomethyl)glycinate |
| XXII | Octyl-N-(phosphonomethyl)glycinate |
| XXIII | Decyl-N-(phosphonomethyl)glycinate |
| XXIV | Dodecyl-N-(phosphonomethyl)glycinate |
| XXV | Chloroethyl-N-(phoshonomethyl)glycinate |
| XXVI | Mono(methylamine) salt of N-phosphonomethylglycine |
| XXVII | Mono(diisopropylamine) salt of N-phosphonomethylglycine |
| XXVIII | Mono(diethanolamine) salt of N-phosphonomethylglycine |
| XXIX | Mono(triethylamine) salt of N-phosphonomethylglycine |
| XXX | Mono(pyridine) salt of N-phosphonomethylglycine |
| XXXI | Mono(aniline) salt of N-phosphonomethylglycine |
| XXXII | Bis(N-phosphonomethylglycine) hydrochloride hydrate |

The compositions of this invention are extremely useful in minimum tillage methods of crop culture. Thus, for example, in those instances where it is desirable to plant a sodded or otherwise vegetated acreage with corn or the like without plowing or otherwise mechanically preparing a seed bed, the crop seed can be drill planted in combination with a prior or subsequent application of a composition of this invention to kill undesired growing vegetation provided that the composition is applied before the emergence of the crop plant.

The compositions of this invention are also useful in sod (turf, alfalfa, pasture, etc.) renovation or conversion procedures. Thus, for example, in situations where a sod or parts thereof has become overgrown with undesirable plant species, the plants in said area can be sprayed with a phytotoxic composition of this invention to control all growing plants and from about 2 to 24 hours later depending upon weather conditions etc., the desired species can be seeded into the dying vegetation. Where a seed bed is to be prepared about 2 to 3 weeks should elapse between treatment and seed bed preparation, in order to provide sufficient time for the composition to be assimilated by all parts of the undesired plants. In an alternate method of sod renovation, the area can be seeded and immediately sprayed with a composition of this invention. In either method, the seeds fall among the vegetation and as the sprayed plants wither and die, they act as a mulch and moisture retaining layer in which the seeds can germinate. This method is particularly useful in the spot renovation of lawns or golf greens or fairways since the herbicidal effect of the compositions of this invention is greatly decreased or totally inactivated by contact with soil. Thus, seeds which are in the soil can germinate and grow without any apparent effects from the spraying of the unwanted plants prior to the time that the seed actually germinates.

The compositions of this invention provide a wide spectrum of weed control and are also extremely useful as general herbicides as well as in controlling unwanted plants in orchards, tree farms, and various crops. For example, it has been found that by directing a spray of the compositions of this invention at the unwanted plants while essentially preventing such spray from contacting the leaves of trees, that such unwanted plants are controlled while there is no apparent injury to the trees. In such directed spraying, the spray can fall on the woody portion of the fruit tree or other tree without any apparent effect. Thus, the directed spray method of control is useful with crops such as plantation crops, i.e. rubber, coffee, bananas, tea, etc. and in orchards such as citrus fruits, apples, peaches, pears, nuts, olive, in vineyards and in bramble crops and in nursery crops to control the undesired plants; and in crops such as cotton, soybeans, sugarcane and the like.

The compositions of this invention are also useful for control of weeds between cropping seasons, for the renovation of stale seed beds and the like.

In applying the compositions of this invention to the plants which it is desired to control, it has been found to be desirable that the plant be emerged from the ground and even more desirable, that the plant be at least at the 2 leaf stage for maximum effect. It has been found that when the plants to be controlled have a portion of their growth above the ground or water, and the above-ground or above-water portion of the plant contacted with the herbicidal compositions of this invention at appropriate rates, the herbicide is translocated to kill such plant parts which are below the ground or water surface.

One can obtain limited selectivity in crops such as cotton, soybeans, sugar cane and like crops by directing the spraying of a composition of this invention at a selected concentration on vegetation around the base of such plants with minimal spray contact with the leafy portions of such crop plants. The directed spraying can be done with or without a protective device to prevent contact of the spray with the leaves of such crop plants.

A non-exhaustive list of some of the plant species which are controlled by the compositions of this invention, in addition to those shown in Table I, are set forth below:

| | |
|---|---|
| Medicago sativa | Poa annua |
| Lolium multiflorum | Hordeum vulgare |
| Hordeum murinum | Galium aparine |
| Alopecurus myosuroides | Bracharia platyphylla |
| Agrostis tenuis | Plantago lanceolata |
| Phaseolus vulgaris var. humilies | Mollugo verticillata |
| Daucus carota var. sativa | Portulaca oleracea |
| Stellaria media | Zea mays |
| Agrostemma githago | Spergula arvensis |
| Gossypium hirsutum | Saponaria vaccaria |
| Agropyron cristatum | Cucumis sativus |
| Rumex crispus | Eriochloa gracilis |
| Paspalum dilatatum | Camelina microcarpa |
| Amsinckia intermedia | Linum usitatissimum |
| Setaria faberil | Ambrosia trifida |
| Setaria viridis | Lithospermum officinale |
| Secale cereale | Sisymbrium officinale |
| Lamium amplexicaule | Brassica juncea |
| Datura stramonium | Avena sativa |
| Arachis hypogaea | Pisum sativum |

-continued

| | |
|---|---|
| Solanum tuberosum | Sida spinosa |
| Cyperus rotundus | Polypogon monspeliensis |
| Raphanus sativus | Ambrosia artemisiifolia |
| Rottboellia exaltata | Brassica napus |
| Beta vulgaris | Oryza sativa |
| Amaranthus retroflexus | Poa trivialis |
| Cenchrus pauciflorus | Rumex acetosella |
| Cassia obtusifolia | Andropogon saccharoides |
| Zea mays var. saccharata | Fagopyrum tataricum |
| Lycopersicon esculentum | Citrullus vulgaris |
| Sorghum bicolor | Brassica kaber var. pinnatifida |
| Avena fatua | Erigeron canadensis |
| Plantago lanceolata | Trifolium pratense |
| Dactylis glomerata | Daucus carota |
| Solanum carolinense | Solanum elaegnifolium |
| Franseria tomentosa | Poa pratensis |
| Festuca arundinaceae | Festuca rubra |
| Agrostis spp | Cynodon dactylon |
| Panicum dichotomiflorum | Commelina diffusa or communis |
| Pennisetum clandestinum | Paspalum spp |
| Mikania cordata | Ottochloa nodosa |
| Imperata cylindrica | Axonopus compressus |
| Scleria bancara | Commellina nudiflora |
| Eleucine indica | |

The phytotoxicant compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent, particularly with the highly water-soluble glycine salts such as the alkali metal salts and amine and ammonium salts. With these derivatives, solutions containing as high as five pounds or more of active materials per gallon can be readily prepared.

The phytotoxicant compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example fertilizers, phytotoxicants and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxyl phenyl-N,N-dimethylurea
1,1'-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanecarsonate
N-(1,1-dimethylpropynyl)-3,5-dichlorobenzamide Fertilizers useful in combination with the active ingredients include for example ammonium nitrate, urea, potash, and superphosphate.

When operating in accordance with the present invention, effective amounts of the glycines are applied to above ground portions of plants. The application of liquid and particulate solid herbicidal compositions to above ground portions of plants can be carried out by conventional methods, e.g. power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.01 to about 20 or more pounds per acre. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e. a phytotoxic or herbicidal amount. It is believed that one skilled in the art can readily determine from the teachings of this specification, including examples, the approximate application rate.

The compositions of this invention are also useful as harvesting aids in many crops. Thus, for example, the crop could be sprayed with the compositions of this invention to reduce the bulk of unwanted material and make the harvesting of the crops easier. Such crops are for example, peanuts, soybeans, and root crops such as potatoes, sugar beets, red beets, and the like.

Although the invention is described with respect to specific modifications, the details thereof are not to be construed as limitations except to the extent indicated in the following claims.

What is claimed is:

1. A phytotoxic composition comprising an inert adjuvant and an effective amount of a compound of the formula

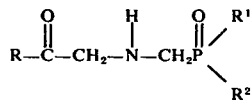

wherein R is —OR³ wherein R³ is selected from the group consisting of monovalent hydrocarbon groups, monovalent hydrocarbon-oxyhydrocarbon groups each containing from 1 to 18 carbon atoms, halogenated monovalent hydrocarbon groups, halogenated monovalent hydrocarbonoxyhydrocarbon groups each containing from 1 to 18 carbon atoms and from 1 to 3 halogens,

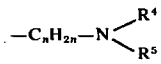

groups wherein $n$ is from 1 to 4 and R⁴ and R⁵ are independently selected from the group consisting of hydrogen, alkyl and hydroxyalkyl having 1 through 4 carbon atoms, alkenyl having 2 through 4 carbon atoms, R¹ and R² are each independently selected from the group consisting of —OH; —OR³ wherein R³ is as above defined and —OR⁶ wherein R⁶ is a salt-forming cation selected from the group consisting of cations of alkali metals, alkaline earth metals, copper, zinc, manganese, nickel, ammonium, organic ammonium, provided that when the organic group is aryl the ammonium salt is a primary amine salt, and mixtures of such salts, provided that no more than two of R, R¹ or R² can be —OR³.

2. A composition in accordance with claim 1 wherein R is —OR³ and R³ is an alkyl group containing from 1 through 18 carbon atoms, alkenyl having from 2 through 8 carbon atoms, alkynyl having 2 through 8 carbon atoms, haloalkyl, haloalkenyl or haloalkynyl having from 1 through 18 carbon atoms and from 1 through 3 halogens and R¹ and R² are —OH, or —OR⁶.

3. A composition in accordance with claim 2 in which R is —OR³ wherein R³ is alkyl or chloroalkyl.

4. A composition in accordance with claim 1 in which the compound is methyl-N-phosphonomethyl-glycinate.

5. A composition in accordance with claim 1 in which the compound is ethyl-N-phosphonomethyl-glycinate.

6. A composition in accordance with claim 1 in which the compound is chloroethyl-N-phosphonomethylglycinate.

7. A method which comprises contacting a plant with a phytotoxic amount of a compound of the formula

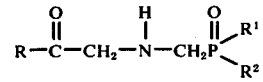

wherein R is —OR³ wherein R³ is selected from the group consisting of monovalent hydrocarbon groups, monovalent hydrocarbon-oxyhydrocarbon groups each containing from 1 to 18 carbon atoms, halogenated monovalent hydrocarbon groups, halogenated monovalent hydrocarbonoxyhydrocarbon groups each containing from 1 to 18 carbon atoms and from 1 to 3 halogens,

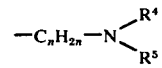

groups wherein $n$ is from 1 to 4 and R⁴ and R⁵ are independently selected from the group consisting of hydrogen, alkyl and hydroxyalkyl having 1 through 4 carbon atoms, alkenyl having 2 through 4 carbon atoms, R¹ and R² are each independently selected from the group consisting of —OH; OR³ wherein R³ is as above defined and —OR⁶ wherein R⁶ is a salt-forming cation selected from the group consisting of cations of alkali metals, alkaline earth metals, copper, zinc, manganese, nickel, ammonium, organic ammonium, provided that when the organic group is aryl the ammonium salt is a primary amine salt, and mixtures of such salts, provided that no more than two of R, R¹ or R² can be —OR³.

8. The process of claim 7 wherein R is OR³ and R³ is an alkyl group containing 1 through 18 carbon atoms, alkenyl having 2 through 8 carbon atoms, alkynyl having 2 through 8 carbon atoms, haloalkyl, haloalkenyl or haloalkynyl having from 1 to 18 carbon atoms and from 1 through 3 halogens and R¹ and R² are —OH or —OR⁶.

9. The process of claim 8 in which R is OR³ wherein R³ is alkyl or chloroalkyl.

10. The process of claim 7 in which the compound is methyl-N-phosphonomethyl glycinate.

11. The process of claim 7 in which the compound is ethyl-N-phosphonomethyl glycinate.

12. The process of claim 7 in which the compound is chloroethyl-N-phosphonomethyl glycinate.

* * * * *